United States Patent [19]

Inoue et al.

[11] Patent Number: 4,943,385
[45] Date of Patent: Jul. 24, 1990

[54] THIOETHER COMPOUND AND LIQUID CRYSTAL COMPOSITION

[75] Inventors: Hiromichi Inoue; Takashi Inukai; Shinichi Saito; Kazutoshi Miyazawa; Kouji Ohno, all of Yokohamashi, Japan

[73] Assignee: Chisso Corporation, Osaka, Japan

[21] Appl. No.: 206,372

[22] Filed: Jun. 14, 1988

[30] Foreign Application Priority Data

Jun. 15, 1987 [JP] Japan .................. 62-148427

[51] Int. Cl.$^5$ .................. C09K 19/34; C09K 19/12
[52] U.S. Cl. .................. 252/299.61; 252/299.65; 252/299.67; 560/18; 544/298; 544/335; 546/301; 546/342; 350/350 S; 558/404; 558/416
[58] Field of Search ............ 252/299.01, 299.61, 252/299.65, 299.67; 560/18; 544/298, 335; 546/301, 342; 350/350 S, 350 R; 558/404, 416

[56] References Cited

U.S. PATENT DOCUMENTS

| | | | |
|---|---|---|---|
| 4,613,209 | 9/1986 | Goodby et al. | 350/350 S |
| 4,689,176 | 8/1987 | Inoue et al. | 252/299.65 |
| 4,780,242 | 10/1988 | Miyazawa et al. | 252/299.65 |
| 4,826,621 | 5/1989 | Terashima et al. | 252/299.61 |
| 4,826,979 | 5/1989 | Kano | 544/224 |
| 4,834,907 | 5/1989 | Inoue et al. | 252/299.65 |
| 4,874,545 | 10/1989 | Heppke et al. | 252/299.61 |
| 4,876,028 | 10/1989 | Hemmerling et al. | 252/299.61 |

FOREIGN PATENT DOCUMENTS

| | | |
|---|---|---|
| 3434335 | 3/1986 | Fed. Rep. of Germany .................. 252/299.61 |
| 54-100341 | 8/1979 | Japan . |
| 54-144331 | 11/1979 | Japan . |

OTHER PUBLICATIONS

Demus et al. (ed.), Flussige Kristalle in Tabellen II, p. 387 (1984).
Gray et al. (ed.), Liquid Crystals & Plastic Crystals, vol. 1, pp. 142-143 (1974).

Primary Examiner—John F. Terapane
Assistant Examiner—Richard Treanor
Attorney, Agent, or Firm—Wenderoth, Lind & Ponack

[57] ABSTRACT

A liquid crystalline compound useful as a component of liquid crystal compositions for liquid crystal display elements, exhibiting ferroelectric liquid crystal phases over a broad temperature range including room temperature, and a liquid crystal composition containing the same are provided. The compound is a thioether compound of the formula

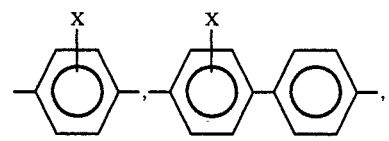

wherein $R^1$ is a 2-10C alkyl; $R^2$ is methyl or ethyl; but the carbon number of $R^1$ is always larger than that of $R^2$; A is

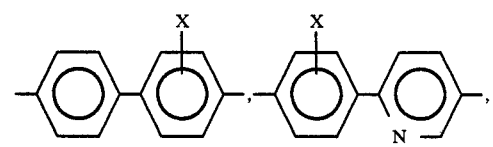

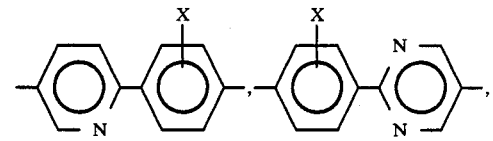

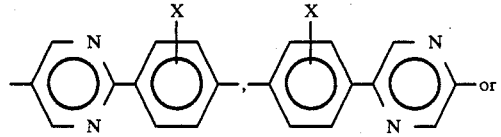

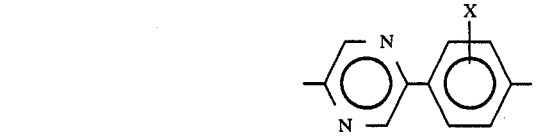

wherein X is H, halogen or CN; Y is a 1-18C alkyl or alkoxy; l is 1 or 2; and * indicates optically active carbon atom.

6 Claims, No Drawings

THIOETHER COMPOUND AND LIQUID CRYSTAL COMPOSITION

BACKGROUND OF THE INVENTION

1. Field of the Invention

This invention relates to a liquid crystalline compound and a liquid crystal composition containing the same, each useful in the fields of devices such as liquid crystal display elements and liquid crystal light-switching elements. More particularly it relates to a novel liquid crystalline compound having an optically active group and a liquid crystal composition containing the same and exhibiting a chiral nematic phase and cholesteric phase.

2. Description of the Related Art

It is well known that the importance of optically active substances contained in liquid crystal compositions used for electrooptical elements utilizing liquid crystal phases, namely, liquid crystal display elements or liquid crystal light-switching elements, consists in the usefulness of the substances as components of compositions exhibiting
 (i) cholesteric phase (chiral nematic phase) and
 (ii) chiral smectic phase.

It is also known that as to cholesteric phase (Ch phase), it is possible to constitute the phase in compounds exhibiting Ch phase by themselves as main components, and it is also possible to constitute the phase by adding an optically active substance to substances exhibiting a nematic phase, and further, in the latter case, it is not necessary that the added optically active substance exhibit a liquid crystal phase by itself. Further, it is also known that Ch phase is not only utilized for display elements utilizing cholestericnematic phase transition, but also utilized in place of nematic phase in order to prevent occurrence of the so-called reverse domain in TN cell (Twisted Nematic cell). Further, the importance of optically active substances as a component constituting cholesteric liquid crystal compositions in STN mode (a mode of making the twist angle of liquid crystals about 180° to 270°) which is one of the relatively new display modes has been more and more increasing.

On the other hand, electrooptical elements using chiral smectic liquid crystals have recently been noted. This new mode utilizes the ferroelectric properties of liquid crystals and according to this mode, there is a notable improvement in the response rate (see Clark et al, Applied Phys. lett., 36, 899 (1980)). This display mode utilizes chiral smectic phases such as chiral smectic C phase (hereinafter abbreviated as SC* phase). It is known that phases exhibiting ferroelectric properties are not limited to SC* phase, and chiral smectic F, G, H, I phase and the like also exhibit ferroelectric phases. When these ferroelectric liquid crystals are utilized for display elements, liquid crystal materials exhibiting ferroelectric liquid crystal phases within a broad temperature range including room temperature have been desired. At present, however, no single compound satisfying such a requirement has been known; hence liquid crystal compositions obtained by combining some compounds together and satisfying the desired specific features as much as possible have been used.

Chiral smectic liquid crystal compositions, as in the case of Ch phase, may be constituted by using compounds exhibiting chiral smectic phase by themselves as main components, but they may also be constituted by adding optically active substances to compounds exhibiting smectic phase, and in this case, too, it is not necessary that the added optically active substances exhibit liquid crystal phases by themselves.

SUMMARY OF THE INVENTION

The present inventors have searched for various compounds in order to find liquid crystalline compounds useful as a component of liquid crystal compositions as described above and as a result have achieved the present invention. In addition, the liquid crystalline compound referred to herein includes not only compounds whose liquid crystal state can be observed by themselves, but also substances which, even though having no liquid crystal state which can be observed by themselves, have a chemical structure similar to those of the above compounds and are useful as an additive as described above.

The present invention in a first aspect resides in a thioether compound expressed by the formula

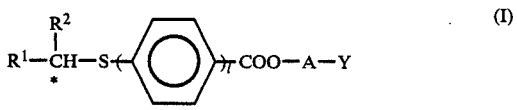

wherein $R^1$ represents an alkyl group of 2 to 10 carbon atoms; $R^2$ represents a methyl group or ethyl group; but the carbon number of $R^1$ is always larger than that of $R^2$; A represents any one of

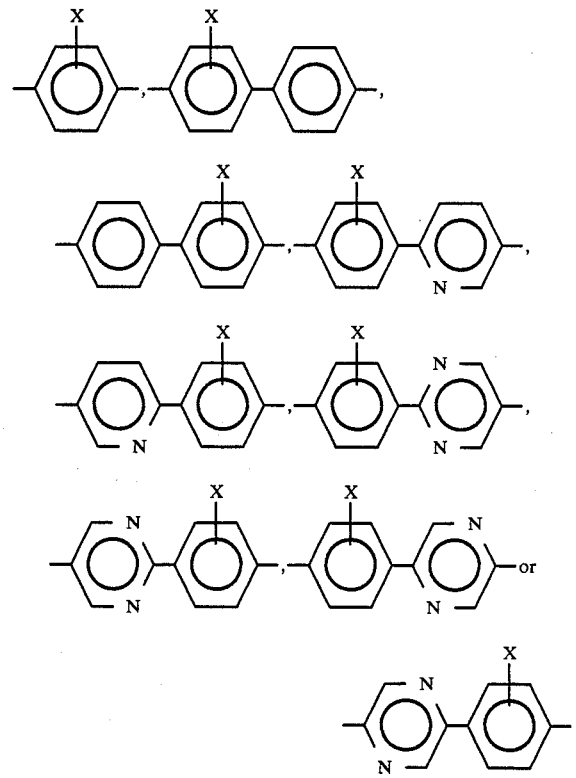

wherein X represents hydrogen atom, a halogen atom or cyano group; Y represents an alkyl group or an alkyloxy group each of 1 to 18 carbon atoms, hydrogen atom, a halogen atom or cyano group; ( represents 1 or 2; and * indicates that the carbon atom having this symbol * attached thereon is optically active.

The present invention in a second aspect resides in a liquid crystal composition containing at least one of the above compounds of the formula (I), particularly a chiral smectic liquid crystal composition.

The present invention in a third aspect resides in an electrooptical element, i.e. device, containing the above liquid crystal composition.

DETAILED DESCRIPTION OF PREFERRED EMBODIMENTS

Representative examples of the compound of the formula (I) exhibit phase transition points as shown below in Table 1.

The compound of the present invention is characterized by having a moiety

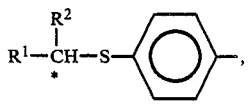

i.e. a thiophenyl group the sulfur atom of which is bonded directly to an optically active carbon atom. The present inventors have previously disclosed a substance having a moiety

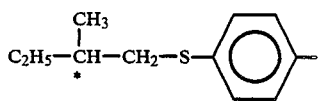

in Japanese patent application laid-open No. Sho 54-100,341/1979. On the other hand, the substance of the present invention has the following superior specific features:

TABLE 1

| Sample No. | In formula (I) $R^1-\overset{R^2}{\underset{*}{CH}}-$ | 1 | A | Y | C | Phase transition points (°C.) SC* | SA | ch | I |
|---|---|---|---|---|---|---|---|---|---|
| 1 | $\underset{*}{C_6H_{13}\overset{CH_3}{\underset{|}{CH}}-}$ | 1 |  | $C_8H_{17}$ | ● 80.0 SB | ● 81.5 | ● 90.2 | — | ● 109.6 ● |
| 2 | " | 1 | " | $OC_6H_{13}$ | ● 97.4 | (● 97.1) | ● 108.5 | — | ● 141.4 ● |
| 3 | " | 1 | " | $OC_8H_{17}$ | ● 76.0 | ● 81.1 | ● 115.3 | — | ● 136.7 ● |
| 4 | " | 1 | " | $OC_9H_{19}$ | ● 80.0 | ● 81.0 | ● 117.3 | — | ● 132.8 ● |
| 5 | " | 1 | " | $OC_{10}H_{21}$ | ● 80.5 | ● 82.0 | ● 119.5 | — | ● 132.1 ● |
| 6 | " | 1 | " | CN | ● 64.0 | — | — | ● 144.4 | ● 165.0 ● |
| 7 | " | 1 | " | F | ● 109.5 | — | — | ● 110.0 | ● 111.0 ● |
| 8 | " | 1 |  | $C_8H_{17}$ | ● 56.8 | — | — | — | ● 95.6 ● |
| 9 | " | 1 |  | $C_8H_{17}$ | ● 51.0 | — | — | — | ● 87.5 ● |
| 10 | " | 1 | 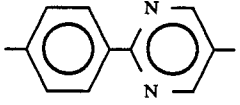 | $C_9H_{19}$ | ● 60.0 | (● 52.6) | ● 76.8 | — | ● 110.0 ● |
| 11 | " | 1 | 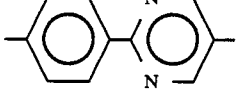 | $C_8H_{17}$ | ● 51.4 | — | — | — | ● 87.4 ● |
| 12 | " | 1 | 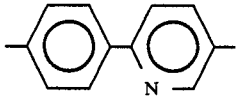 | $C_5H_{11}$ | ● 12.0 | — | — | — | ● |
| 13 | " | 1 | " | $OC_5H_{11}$ | ● 32.0 | — | — | — | ● |
| 14 | " | 1 | " | CN | ● 40.5 | — | — | — | ● |

The first specific feature consists in that when the substance is added to a nematic liquid crystal, the capability of inducing the cholesteric twist structure of the resulting mixture increases up to about twice that of the liquid crystal. In other words, for forming the same cholesteric pitch, the quantity of the substance of the present invention added need only be about one-half of that of the substance of

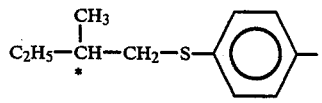

type. This effect is considered to be due to the fact that the optically active center is in a position closer to the benzene ring.

Another specific feature of the compound of the present invention consists in that the cholesteric pitch induced when the compound is added to a nematic liquid crystal has a negative temperature coefficient. Namely, the cholesteric pitch decreases with increase of temperature, contrary to conventional optically active substances. The usefulness of such a specific feature has recently been reported in detail by the present inventors (Proceeding of Japan Display, 1986, p. 286), but among optically active substances having such a specific feature, those which are sufficiently stable have only been nothing but compounds having a moiety

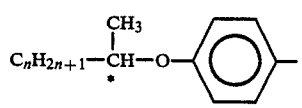

disclosed therein. The compound of the present invention corresponds to a sulfur-analog thereof (S-analog), and it is interesting that the temperature coefficient of the cholesteric pitch is negative like the oxygen-analog (O-analog). A superior specific feature of the S-analog consists in that the capability of inducing the cholesteric twist structure is about three times that of the O-analog. Namely, for inducing the same cholesteric pitch, the quantity thereof added need only be about ⅓ of that of the O-analog. Since a small quantity thereof is sufficient, all the substances of the present invention, and even those having no liquid crystal phase by themselves, effectively function as an additive.

On the other hand, as illustrated in Table 1, some compounds among those of the present invention exhibit chiral smectic phases (particularly, chiral smectic C phase) and these compounds are particularly preferred as a component of liquid crystal compositions for electrooptical elements utilizing ferroelectric properties. However, all the compounds of the present invention may be used as an additive to smectic phases (particularly, smectic C phase or chiral smectic C phase). The compounds of the present invention generally have an adequately low melting point and a high compatibility into various smectic C phases. The smectic C phases are exhibited in a mixture of known compounds exhibiting smectic C phase. It has been known since several years ago that when an optically active compound is added to a substance exhibiting a smectic C phase, the resulting mixture exhibits a chiral smectic C phase.

The compound of the formula (I) of the present invention may be prepared according to a previously known standard preparation directed to esters of aromatic carboxylic acids with aromatic phenols.

Namely, the compound may be prepared by reacting an aromatic carboxylic acid expressed by the formula

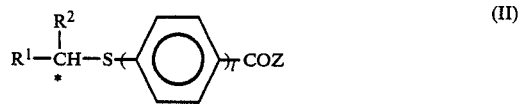

(wherein Z=OH), its reactive derivative (a compound of the formula (II) wherein Z=Cl, Br or a lower alkyloxy group, particularly methoxy group) or an acid anhydride corresponding thereto, with a phenolic or hetero-substituted phenolic compound expressed by the formula $$XO-A-Y \qquad (III)$$

(wherein X=H) or its alkali metal phenolate or alkaline earth metal phenolate (a compound of the formula (III) wherein X=Na, ½Ca or the like), if desired, in the presence of an organic solvent and in the presence of a conventional esterification catalyst. Concretely, the preparation mentioned later in Examples is usually most simple and preferred.

Of the starting compounds,

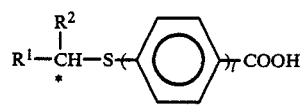

may be suitably prepared through the following route:

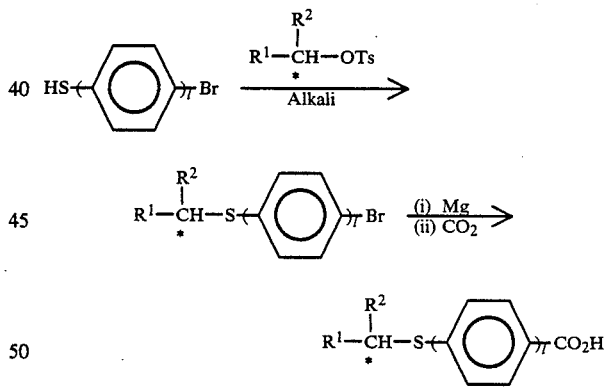

In the case of l=2, the following route is suitable:

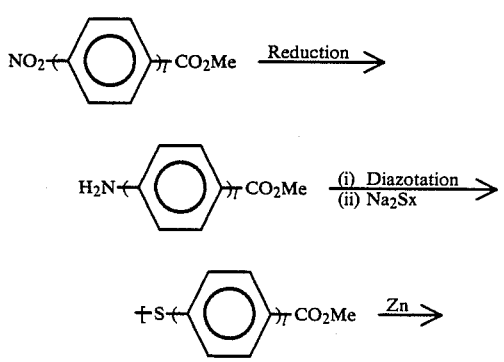

-continued

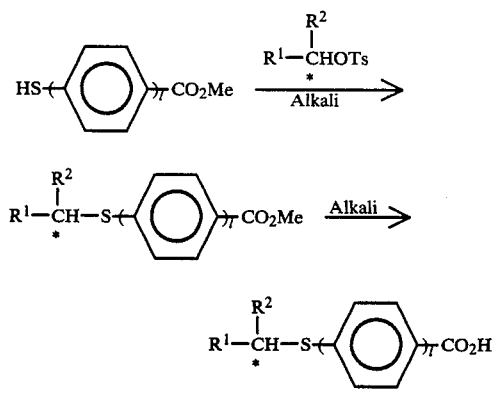

Another of the starting compounds, HO-A-Y, is mostly known and those which are not known may be prepared according to a known chemical means. Compounds of

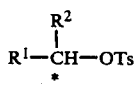

(optically active alcohol toluenesulfonates) may be prepared from an optically active alcohol and toluenesulfonyl chloride according to a known method. Those of the above formula wherein $R^2$ represents a methyl group are all known, and as to those of the formula wherein $R^2$ represents an ethyl group, for example, those obtained by resolving a racemic 3-alkanol into an optically active substance with lipase according to ester exchange reaction may be preferably used.

The compound and composition of the present invention will be described in more detail by way of Examples.

EXAMPLE 1

Preparation of S-4-(1-methylheptylthio)-benzoic acid 4-octylbiphenylyl ester (a compound of the formula (I) wherein $R^1=C_6H_{13}$, $R^2=CH_3$, $l=1$,

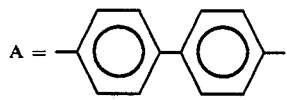

and $Y=C_8H_{17}$; Sample No. 1)

(i) Preparation of S-p-(1-methylheptylthio)-bromobenzene

R-1-methylheptyl p-toluenesulfonate (73.7 g) was dropwise added to a mixed solution of p-bromophenol (49 g), KOH (14.5 g) and ethanol (250 ml), followed by heating the mixture under reflux for 2 hours, distilling off ethanol, extracting the residue with toluene, washing the resulting solution with an alkali aqueous solution and further with water and distilling it under reduced pressure (160°–163°/4 mmHg) to obtain the objective compound (48.1 g).

$[\alpha]_D^{25°} = -3.8°$ (in ethanol).

In this reaction, it is considered that Walden inversion occurs to form S type thio ether from R type tosylate and R type thio ether from S type tosylate.

(ii) Preparation of S-p-(1-methylheptylthio)-benzoic acid

The thio ether (47 g) obtained above in the step i) was reacted with metallic Mg (4.5 g in anhydrous tetrahydrofuran (200 ml) to obtain a tetrahydrofuran solution of S-p-(1-methylheptylthio)phenylmagnesium bromide, which was then poured on solid carbon dioxide (dry ice) pieces, followed by vaporizing excess solid carbon dioxide, adding water, distilling off tetrahydrofuran, acidifying the residue with 6N-hydrochloric acid, subjecting it to extraction with toluene, extracting the objective compound from the toluene layer with 2N NaOH, acidifying the resulting extract solution and recrystallizing the resulting oily substance from hydrous ethanol to obtain the objective compound (m.p.: 58.0°-58.5° C.).

Angle of rotation $[\alpha]_D^{28°} = -14.4°$ (in ethanol)

In the same manner, R-p-(1-methylheptylthio)benzoic acid, R-p-(1-methylbutylthio)-benzoic acid, S-p-(1-methylpentylthio)-benzoic acid, R-p-(1-ethyl-heptylthio)-benzoic acid, etc. may be prepared.

(iii) Preparation of the captioned compound

S-p-(1-methylheptylthio)-benzoic acid (2.8 g) prepared above in the step ii) was heated together with excess thionyl chloride under reflux to obtain an acid chloride, which was then reacted with 4'-octyl-4-hydroxybiphenyl (3.3 g) in pyridine, followed by passing a toluene solution of the reaction material through a chromatographic column filled with activated alumina for decoloration and recrystallizing the material from ethanol to obtain the objective product. Its phase transition points were as follows:

C-$S_B$ point: 80.0° C., $S_B$-$S_C^*$ point: 81.5° C.,
$S_C^*$-Ch point: 90.2° C., and Ch-I point: 109.6° C.

EXAMPLE 2

Preparation of S-4-(1-methylheptylthio)-benzoic acid 4-(6'-octyl-2'-pyridinyl)-phenyl ester (a compound of the formula (I) wherein $R^1=C_6H_{13}$, $R^2=CH_3$, $l=1$,

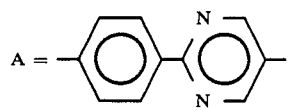

and $Y=C_8H_{17}$; Sample No. 8)

S-4-(1-methylheptylthio)-benzoic acid (2.8 g) obtained above in the step ii) of Example 1 as a raw material was reacted with 4-(6'-octyl-2'-pyridinyl)-phenol (3.3 g), followed by treating the resulting material in the same manner as in the step iii) of Example 1 and recrystallizing from ethanol to obtain the objective compound (1.8 g). Its phase transition points were C-Ch* point: 56.8° C. and Ch-I point: 95.6° C.

EXAMPLES 3–6

Compounds of Sample Nos. 1, 3, 4 and 5, each in one % by weight, were each dissolved in a commercially available nematic liquid crystal, ZLI-1132 (tradename of a product made by Merck Company), and the respective cholesteric pitches (unit: μm) were measured at various temperatures. The results are shown in Table 2.

TABLE 2

| | Sample No. | Temperature measured | | | |
| --- | --- | --- | --- | --- | --- |
| | | 20° C. | 30° C. | 40° C. | 50° C. |
| Example 3 | 1 | 36.9 | 34.0 | 30.1 | 27.6 |
| Example 4 | 3 | 37.4 | 33.9 | 30.4 | 27.8 |
| Example 5 | 4 | 33.8 | 30.1 | 27.2 | 24.9 |
| Example 6 | 5 | 36.3 | 32.6 | 29.4 | 26.5 |
| Comp. ex. 1 | 4' | 110 | 87.6 | 74.8 | 65.7 |

Note: Comparative example 4' is directed to O-analog of Sample No. 4.

EXAMPLE 7

Compounds of Sample Nos. 4, 8, 9 and 10, each in an amount of parts by weight (the total: 20 parts by weight) were mixed with 80 parts by weight of a smectic liquid crystal mixture of 2-p-alkoxyphenyl-5-alkyl-pyrimidines (C-Sc point 4° C.; $S_c$-$S_A$ point 65° C.; $S_A$-N point 79° C.; and N-I point 90° C.). The phase transition points of the resulting liquid crystal composition were as follows:

C-$S_c$* point ≠° C. or lower; $S_c$*-$S_A$ point 63° C.; $S_A$-Ch point 68° C.; and Ch-I point 92° C.

Using this liquid crystal composition, a ferroelectric liquid crystal light switching element was prepared. Namely, a PVA coating was prepared on a glass substrate provided with a transparent electrode of indium oxide, followed by rubbing the coating in one direction. A liquid crystal cell was composed so that the respective rubbing directions of two sheets of the resulting glass substrate might be parallel to each other and using glass fibers of 4 mμ in diameter as a spacer, followed by sealing the above liquid crystal composition in the cell. The resulting element was placed between two crossed polarizers and a voltage of 20V was impressed. As a result, change in the intensity of transmitted light was observed. Its response time was about 1.0 m sec and its contrast ratio was 1:15.

What we claim is:

1. A thioether compound expressed by the formula

wherein $R^1$ represents an alkyl group of 2 to 10 carbon atoms; A represents a member selected from the group consisting of

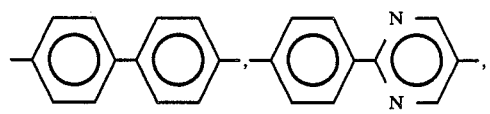

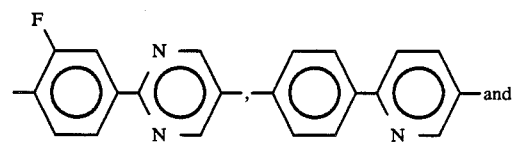

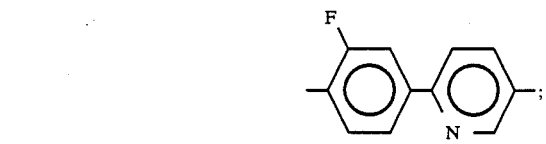

Y represents an alkyl or alkoxy group each of 6 to 12 carbon atoms; and * indicates that the carbon atom having this symbol is optically active.

2. A thioether compound according to claim 1, wherein $R^1$ is $C_6H_{13}$.

3. A liquid crystal composition comprising at least two components at least one of which is a thioether compound as set forth in claim 1.

4. A liquid crystal composition according to claim 3, exhibiting a cholesteric liquid crystal phase.

5. A liquid crystal composition according to claim 3, exhibiting chiral smectic liquid crystal phase.

6. A liquid crystal electrooptical device containing a liquid crystal composition as set forth in claim 3.

* * * * *